United States Patent
Nett et al.

(10) Patent No.: US 9,795,356 B2
(45) Date of Patent: Oct. 24, 2017

(54) SYSTEM AND METHOD OF X-RAY DOSE DISTRIBUTION FOR COMPUTED TOMOGRAPHY BASED ON SIMULATION

(71) Applicant: General Electric Company, Schenectady, NY (US)

(72) Inventors: Brian E. Nett, Waukesha, WI (US); Roy A. Nilsen, Waukesha, WI (US); Grant M. Stevens, Cedarburg, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 980 days.

(21) Appl. No.: 14/132,524

(22) Filed: Dec. 18, 2013

(65) Prior Publication Data
US 2015/0164457 A1 Jun. 18, 2015

(51) Int. Cl.
G06F 17/50 (2006.01)
A61B 6/00 (2006.01)
A61B 6/03 (2006.01)

(52) U.S. Cl.
CPC ............ *A61B 6/542* (2013.01); *A61B 6/032* (2013.01); *A61B 6/545* (2013.01); *A61B 6/482* (2013.01); *G06F 17/5009* (2013.01)

(58) Field of Classification Search
USPC ........................................ 703/2, 18; 600/407
See application file for complete search history.

(56) References Cited

U.S. PATENT DOCUMENTS

| | | | |
|---|---|---|---|
| 9,427,201 B2* | 8/2016 | West ................ | A61B 6/466 |
| 2005/0033151 A1* | 2/2005 | Wu ................... | G01R 33/561 |
| | | | 600/410 |
| 2009/0005668 A1* | 1/2009 | West ................ | A61B 6/466 |
| | | | 600/407 |
| 2011/0234224 A1* | 9/2011 | Bieri ................ | G01R 33/5614 |
| | | | 324/309 |
| 2011/0252248 A1* | 10/2011 | Cameron ......... | G06Q 10/04 |
| | | | 713/300 |
| 2011/0282181 A1* | 11/2011 | Wang .............. | A61B 5/0095 |
| | | | 600/407 |
| 2013/0202079 A1* | 8/2013 | Yu .................. | A61B 6/5258 |
| | | | 378/19 |
| 2014/0336957 A1* | 11/2014 | Hanson ........... | G01J 3/4338 |
| | | | 702/50 |

OTHER PUBLICATIONS

"Synthetic CT Noise Emulation in the Raw Data Domain"; Thomas M. Benson and Bruno K.B. De Man, authors.

(Continued)

*Primary Examiner* — Thai Phan
(74) *Attorney, Agent, or Firm* — Fletcher Yoder, P.C.

(57) ABSTRACT

An imaging system allows for modification of data acquisition parameters, where the parameters affect dose distribution. The system includes a library of exams, and a computer programmed to obtain a set of scanning parameters for image data acquisition and image reconstruction, obtain scan data from the library of exams that is based on a similarity metric for a patient to be scanned, simulate a new scan of the patient using the obtained scan data and using the obtained set of scanning parameters, and generate a new set of scanning parameters based on the simulation.

20 Claims, 4 Drawing Sheets

(56) References Cited

OTHER PUBLICATIONS

"Synthetic CT: Simulating low dose single and dual energy protocols from a dual energy scan"; Adam S. Wang and Norbert J. Pelc, authors. Published by American Association of Physicists in Medicine Sep. 21, 2011.

"Techniques and Applications of Automatic Tube Current Modulation for CT"; Mannudeep Kalra et al., authors. Published in Radiology, vol. 233, No. 3, Dec. 2004.

* cited by examiner

SYSTEM AND METHOD OF X-RAY DOSE DISTRIBUTION FOR COMPUTED TOMOGRAPHY BASED ON SIMULATION

BACKGROUND

This disclosure relates generally to diagnostic imaging and, more particularly, to an apparatus and method of optimizing a scanning protocol to minimize dose.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

During scanning to acquire projection data, it is generally desirable to reduce x-ray dose received by the subject, thus protocols have been developed that reduce x-ray tube power and patient exposure during image data acquisition. Also, gantry speeds in CT imaging generally continue to increase over time, in an effort to capture images in a shorter time period to reduce motion artifacts. Thus, as x-ray tube power is reduced, and gantry speed is increased, the signal itself may correspondingly decrease, which itself can lead to a lower signal-to-noise ratio (SNR). Thus, protocols have been developed to improve data acquisition and image reconstruction based on data having decreased SNR.

For instance, the concept of dose modulation in CT has been used extensively by each of the manufactures in the form of tube current modulation as a function of table position and x-ray tube angle. In both cases the aim is to deliver an ideal tube current such that the image noise remains relatively constant throughout the volume even as the path length for the x-ray at different positions changes. The parameters for the modulation are typically based on assuming the patient is composed of water cylinders, which are estimated from the scout (i.e., single projection) images. While this approach may offer significant advantages compared with un-modulated acquisitions, there is additional optimization in the x-ray dose modulation which could improve image quality or reduce dose. And, in addition to the tube current modulation, other methods for dose modulation include but are not limited to: kVp modulation, aggressive static bowtie filters, dynamic pre-patient collimation, and dynamically pulsing the x-ray source, as examples. Each of these methods provides a different mechanism to modulate the dose delivered through-out the examination.

However, the above techniques, though known, may not result in a protocol that is optimized for a given patient or for a given scanning scenario. More particularly, although scanning protocols are generally known, selected protocols may not account for particulars of a given scenario. That is, a selected or known protocol may not account for patient size, anatomy, or position, as examples. Further compounding protocol selection, a selected or known protocol may not account for a particular task of the scan (i.e., head CT Angiography, lung, or kidney stones). In other words, scanning protocols are generally known, but typically do not take into account specific patient parameters or particulars of a task that is being performed.

Therefore, it would be desirable to optimize a scanning protocol to minimize dose, based on specifics of the patient and the conditions under which the scanning protocol are implemented.

BRIEF DESCRIPTION

Embodiments are directed toward a apparatus and method of optimizing a scanning protocol to minimize dose in a medical imaging system.

According to one aspect, an imaging system allows for modification of data acquisition parameters, where the parameters affect dose distribution. The system includes a library of exams, and a computer programmed to obtain a set of scanning parameters for image data acquisition and image reconstruction, obtain scan data from the library of exams that is based on a similarity metric for a patient to be scanned, simulate a new scan of the patient using the obtained scan data and using the obtained set of scanning parameters, and generate a new set of scanning parameters based on the simulation.

According to another aspect, a method of optimizing scanning parameters for image data acquisition includes selecting a scanning protocol for image data acquisition and image reconstruction, obtaining scan data from a library of exams that is based on a similarity metric for a patient to be scanned, determining whether the scanning protocol achieves a desired optimization by simulating a scan of the patient that is based on the selected scanning protocol and based on the obtained scan data, and generating a new scanning protocol based on the optimization.

According to yet another aspect, a non-transitory computer readable storage medium having stored thereon a computer program comprising instructions, which, when executed by a computer, cause the computer to select a scanning protocol for image data acquisition and image reconstruction, obtain scan data from a library of exams that is based on a similarity metric for a patient to be scanned, determine whether the scanning protocol achieves a desired optimization by simulating a scan of the patient that is based on the selected scanning protocol and based on the obtained scan data, and generate a new scanning protocol based on the optimization.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that disclosed embodiments are equally applicable for use with other multi-slice configurations, or other imaging systems in general, such as an x-ray system on a c-arm or a micro-CT system, as examples. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
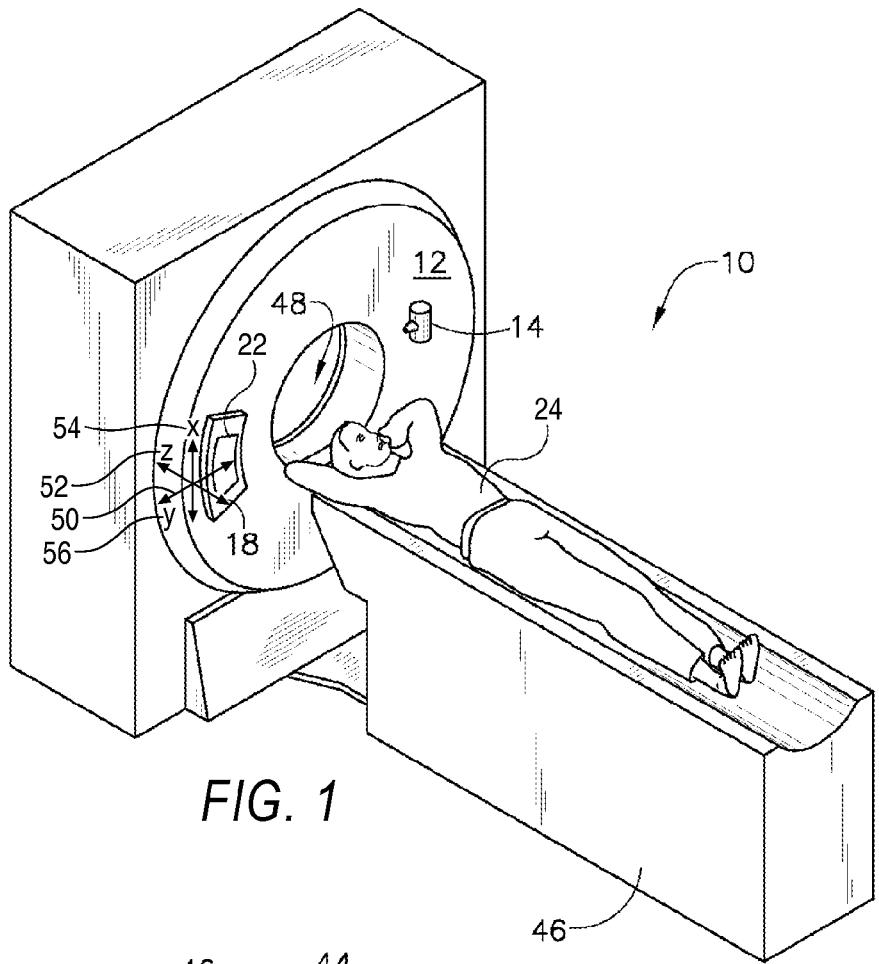
FIG. 1 is a pictorial view of a CT imaging system.
Figure 2:
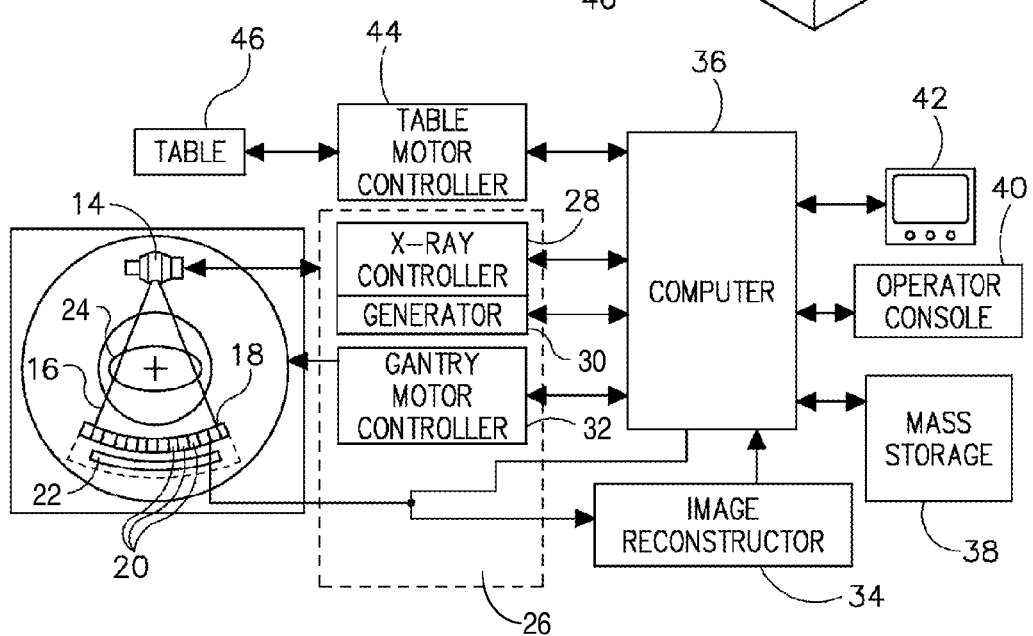
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray tube or source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation 26.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of x-ray source 14 to detector assembly 18.

X-ray source 14, in accordance with present embodiments, is configured to emit x-ray beam 16 at one or more energies. For example, x-ray source 16 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments x-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Techniques to obtain energy sensitive measurements include: (1) scan with two distinctive energy spectra and (2) detect photon energy according to energy deposition in the detector. Such measurements provide energy discrimination and material characterization, and may be used to generate reconstructed images using a base material decomposition (BMD) algorithm. A conventional BMD algorithm is based on the concept that, in an energy region for medical CT, the x-ray attenuation of any given material can be represented by a proper density mix of two materials with distinct x-ray attenuation properties, referred to as the base or basis materials. The BMD algorithm computes two CT images that represent the equivalent density of one of the base materials based on the measured projections at high and low x-ray photon energy spectra, respectively.

Thus, CT image data is obtained that may be from a single or a dual energy application. CT reconstruction is generally a two-step process. The patient is placed on the scanner and an x-ray beam is caused to rotate about the patient, either in a helical or an axial operation. Detectors measure the pattern of radiation (projection) transmitted through the patient. Image reconstruction from the projections is performed using a filtered backprojection (FBP).

Figure 3:
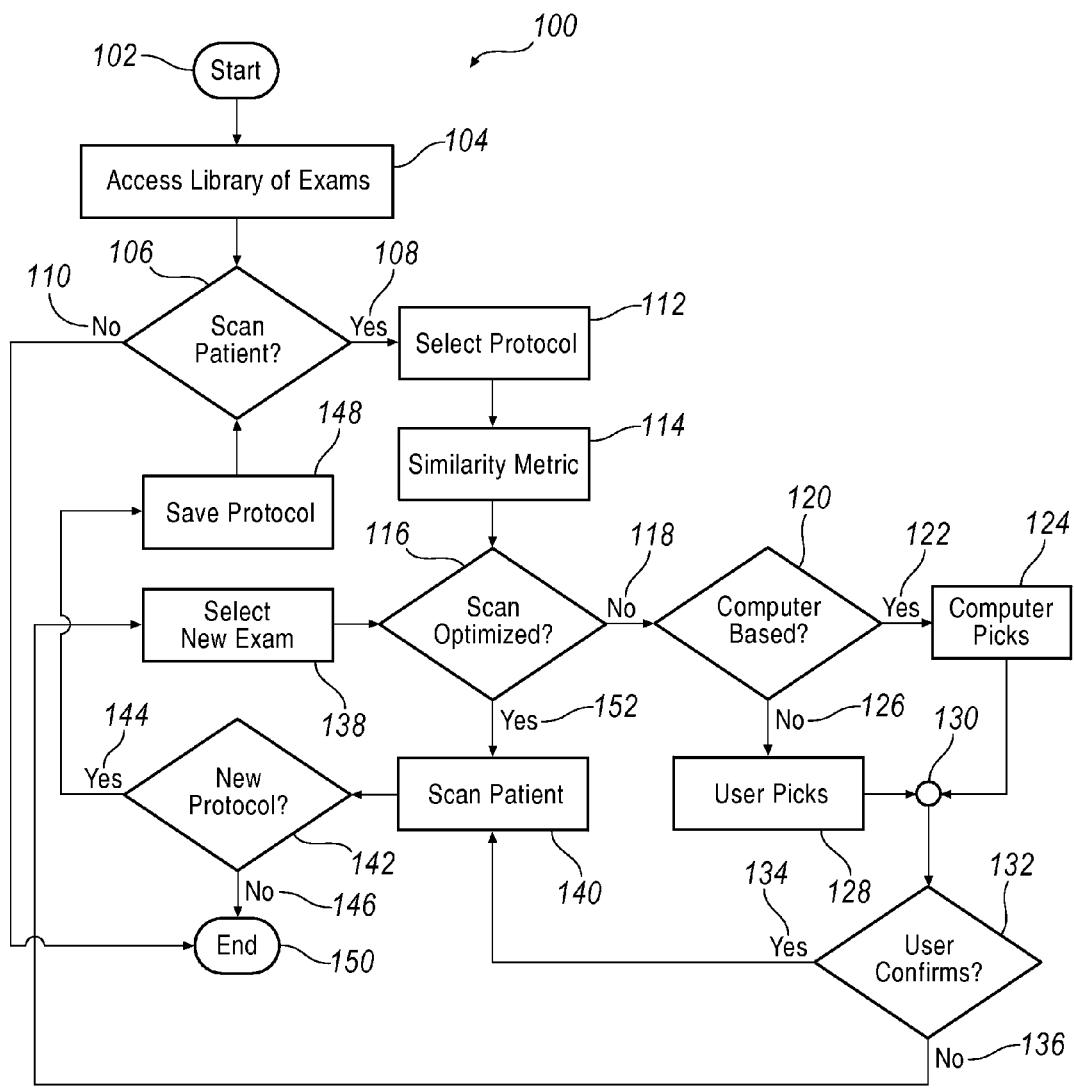
FIG. 3 illustrates a process optimization of dose modulation.

Referring to FIG. 3, a process 100 is disclosed for the use of a simulation of the dose modulation for the purposes of determining the dynamic dose modulation parameters. Starting at step 102, at step 104 a database of a library of exams is accessed that includes protocols for imaging patients under different scenarios. In one example, the library of exams is stored within computer 36 of imaging system 10. However, in another scenario, the library of exams may be stored in an off-site server or a "cloud" storage device that is accessible via the internet. The scenarios for various exams may include but are not limited to patient size, anatomy type (heart, lung, kidney, brain, etc.), position, and task, as examples. The task may be for head CT angiography (CTA), lung, kidney stones, and the like. In one example, a library of relatively high quality CT examinations of different body parts is available and can be used as input for a simulation. The library may also include simulated numerical phantom data or phantom data scanned on a clinical scanner. And, the library may include raw scan data for all of the datasets, such as in the form of a sinogram and before a filtered back-projection is performed.

In general, the library may include scans of patients that have been retained in the library to use for optimizing a scan of a patient. That is, based on a similarity metric, scan data from previous scans may be obtained from the library and used as input, along with scanning parameters that are also obtained, to simulate a new scan of the patient with the intent to optimize the scanning parameters about a given metric.

At step 106, it is determined whether a scan is to be performed 108 or not 110. Thus, in some cases process 100 may be implemented with the purpose of generating a new scanning protocol but without actually proceeding with a scan. If an optimization is to be performed 108, then at step 112 a protocol is selected, that corresponds to a desired examination that was accessed at step 104, and based on a given metric such as optimal dose deposition. A variety of metrics may be considered, such as: dose avoidance to particular areas of anatomy; detectability task; lowest noise in a given region; noise uniformity in a given region, or image quality, as examples. The protocol selected is based on a "like exam" to be performed on the patient, based on the scenario as described above (i.e., patient size, anatomy type [heart, lung, kidney, brain, etc.], position, and task, as examples), and also based on a similarity metric, as will be further described.

At step 114 a similarity metric is determined for the patient, to include imaging information at least in a region of interest (ROI) particular to an anatomy of the patient that is to be imaged. In one example, the similarity metric is based on a scout such as a 2D projection image, or based on a low dose 3D image, and an appropriate input examination may be selected by a similarity measure between either the scout(s) (2D projection images) or based on the initial low dose 3D image volume. In another example, the similarity metric is an image of the patient that was obtained in an earlier imaging session that occurred prior to the current imaging session. In another example, the similarity metric at step 114 is based on one of a patient weight, a body mass index (BMI), and a patient circumference. As another example, a similarity metric may be based on a body mass index (BMI) and may thus be used to select the like exam. In yet another example, a similarity metric may be based on body weight.

Thus, the similarity metric is used to determine or identify an exam from the library of exams that is best suited or assumed likely to yield a scan that is optimized about a given metric. In other words, the similarity metric is used as a basis for selecting the scan data or "like scan" from the library of exams, which serves as a method to decide whether an optimal scan is already selected, or serves as a basis for optimizing the scan parameters to optimize the given metric (i.e., dose deposition) using a simulation.

After the similarity metric is selected, block 116 determines if the scan is optimized based on the given optimization criteria selected (i.e., dose deposition to achieve that dose can be computed based on a realistic simulation of the dose modulation (obviously subject to system constraints such as the mA/ms slew rate etc.). In previous techniques closed form solutions to the problem based on water cylinder approximations have been used. In this disclosed technique, however, the projection data is modified to simulate the changes in dose delivery such as the noise increase which occurs when the mA is reduced in a given view, or the reduction of flux which occurs when a strong pre-patient modulator is selected. Because the physics of the new acquisitions with different modulation protocols is modeled it is also possible to design optimization criteria which include knowledge of the task such as: low contrast lesion insertion in a given region of interest wherein the optimization criteria would be to maximize the ability for a simulated observer to detect the low contrast object. Other tasks could be simulated such as size measurement tasks and given an inserted lesion the optimization criteria could then be to find the dose deposition which enables the most accurate measurements.

Thus, at step 116, it is determined whether the selected protocol (from step 112) is optimized, based at least on the obtained scanning data and also the like exam that was selected based on the similarity metric. If not optimal 118 (that is, if not determined to be dose-optimized based on the input criteria), then a new scanning protocol is generated as will be further described. According to the disclosure, a computer selected or a user or human selected protocol may be generated. Thus, at step 120 a determination is made if a computer selected protocol is to be generated. If so, 122, then at step 124 a computer, such as computer 36 of FIG. 1, generates and selects a candidate imaging protocol. However, if not 126, then a user-selected protocol is generated at step 128. Computer-selected (124) and user-selected (128) protocols are further described, respectively, in FIGS. 4 and 5.

Figure 4:
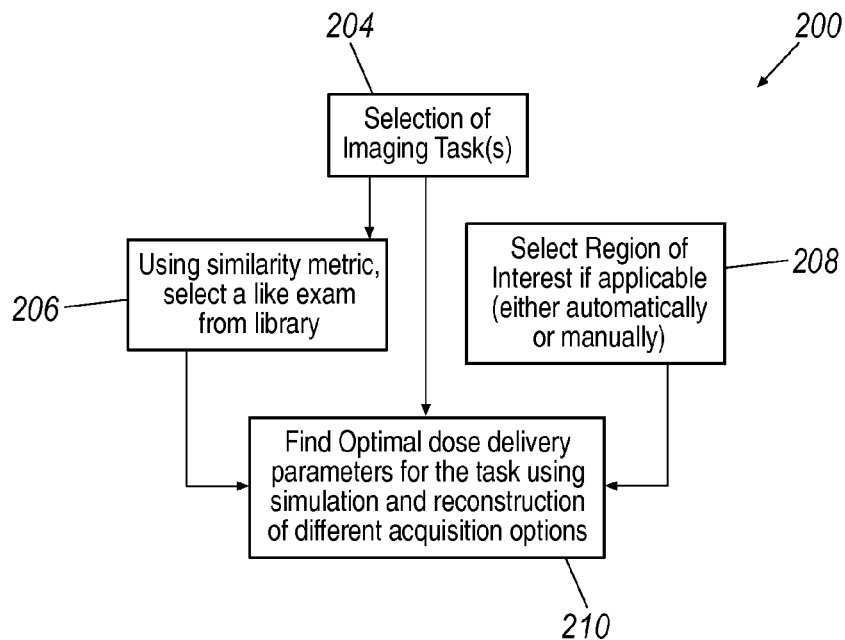
FIG. 4 illustrates a computer-based protocol for optimizing dose modulation.

Referring to FIG. 4, and corresponding to step 124 for a computer-selected protocol, steps 200 include starting with the similarity metric and selection of the imaging task at step 204. Step 204 corresponds generally to step 112, in which an imaging task is defined and a protocol is selected from the library of exams. At step 206, a like exam is selected using a similarity metric from the library of exams. At step 208, a region of interest (ROI) is selected, which may be performed automatically or manually. In automatic mode, the ROI may be determined based on the selected exam, a prior-obtained image, and the type of scan to be performed. In manual mode, the ROI may be selected using a visual-based imaging system that may likewise be based on the selected exam, a prior-obtained image, and the type of scan to be performed, but which also includes manually highlighting the ROI by a user. At step 210, optimal dose delivery parameters for a selected task are found using simulation and reconstruction of different acquisition options, thereby simulating a scan to find optimal dose delivery parameters for the like exam and based on the prior obtained image.

In this example, minimizing dose is not conducted by simply reducing x-ray tube power, or spinning the gantry faster, as examples. Rather, such is performed while also ensuring that adequate imaging data is obtained and having appropriate signal-to-noise ratio (SNR). Thus, in addition one may pose the question: for a given a task what is the lowest dose at which a certain acceptability criteria can be achieved. For instance if success is defined that 100% of simulated lesions with a contrast of 5 HU and size 1 mm×1 mm×1 mm can be detected with a given simulated observer, then a suggestion may be given as to the dose required and the method to best deposit the dose. Thus, in such an instance an objective function may be made arbitrarily complex such as performing a weighted average of the performance of multiple tasks which may occur for a given clinical procedure, as illustrated in the steps of FIG. 4.

Further, while the previous method (corresponding to FIG. 4 and a computer-based selection) enables optimization of the dose delivery and dose level for a given task, the method is reliant on a sufficiently robust optimization criteria for exam. In the case that such criteria are difficult to arrive at, during the process of arriving at these criteria an interactive method may be employed.

Figure 5:
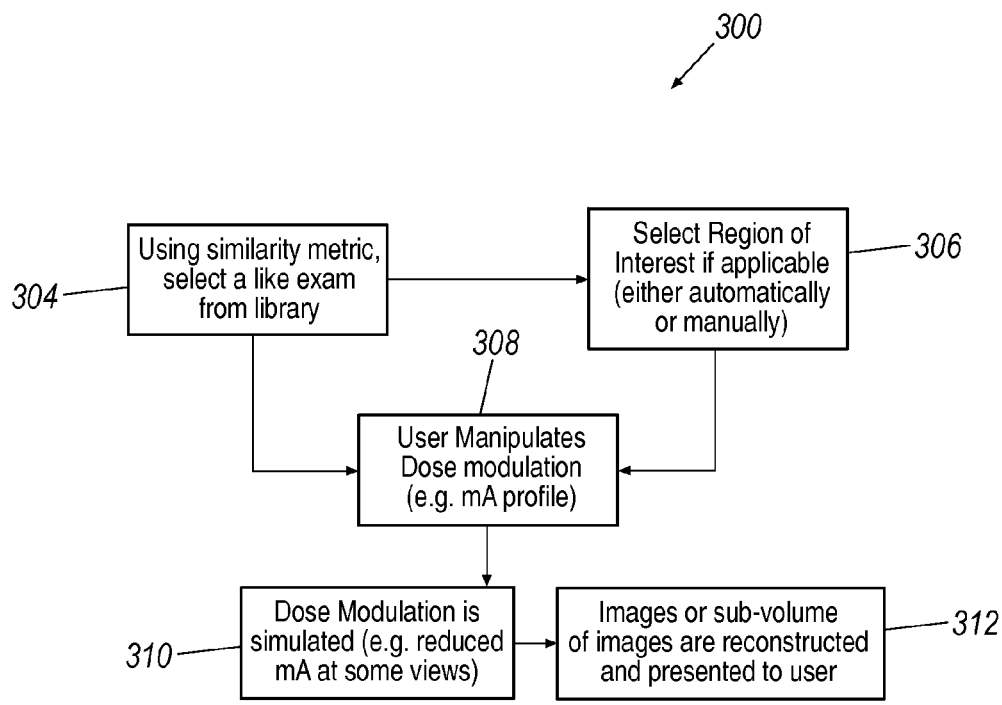
FIG. 5 illustrates a user-based protocol for optimizing dose modulation.

For instance, referring to FIG. 5, for a subset of the image volume different acquisition/reconstruction parameters may be modified in a real-time environment such that the user will get a realistic appreciation of how the change in dose deposition will affect the image quality. In one example, consider the case of an aggressive tube current modulation used to visualize a suspected or known lesion which lies between two regions of high attenuation (e.g. the scapula and humerous of a patient imaged with their arms at their sides). In this case the appropriate similar high dose exam can be selected from the library of exams or from a previous exam of the same patient as described above. In one example, the user may then manipulate the dose distribution (for instance, manipulate the tube current subject to system constraints) and visualize changes in image quality. In this scenario the user would be able to modify the level of noise and observe how the noise correlation affects the image quality before selecting the desired dose deposition protocol.

As such, FIG. 5 illustrates, corresponding to step 128 for a user-selected protocol, steps 300 that include starting with a similarity metric. At step 304, a like exam is selected using a similarity metric from the library of exams. At step 306, a region of interest (ROI) is selected, which may be performed automatically or manually. In automatic mode, the ROI may be determined based on the selected exam, the prior image, and the type of scan to be performed. In manual mode, the ROI may be selected using a visual-based imaging system that may likewise be based on the selected exam, the prior image, and the type of scan to be performed, but which also includes manually highlighting the ROI by a user.

At step 308, a user manipulates dose modulation (e.g., mA profile, kVp, etc.) which is an input to a simulation of dose modulation at step 310. In such fashion, mA may be reduced for some views, while the simulation can reveal when adequate SNR is obtained based thereon. At step 312, images or sub-volumes of images are reconstructed and presented to the user, who is thus able to alter the input parameters and manually optimize dose while maintaining adequate signal quality for image reconstruction. Thus, in user-selected mode, the computer presents results of the simulated scan to the user, and offers the user an opportunity to modify scan parameters in real-time and to present the simulation of the scan to the user so the user can view the modified simulation and modify the scan parameters to generate the new scanning protocol based on the modified simulation.

FIGS. 4 and 5 each represent respective series of inter-related steps that enable dose optimization based on an exam from a library of exams that is selected based on the similarity metric, to obtain an optimal protocol that accomplishes the desired dose optimization. Referring back to FIG. 3, steps 124 and 128 thereby correspond respectively to FIG. 4 and FIG. 5. At point 130, a protocol is thereby available for user confirmation, determined either through computer selection 124 or by user manipulation and selection of parameters 128. At step 132, the user may confirm 134, or not 136, the protocol available for selection at point 130. If the user does not confirm selection 136, then control returns to step 138, where a new exam is selected from the library, and optimization is again determined (based on the newly selected exam), at step 116. However, if the user does confirm 134, then control moves to step 140, in which the scanning parameters of the selected protocol are sent to the scanner, the patient is scanned, and imaging data is acquired. At step 142, if a new protocol has been generated 144, then the new protocol is saved at step 148, and control returns to determine whether another optimization may be performed. If not 146, the process ends at step 150. Thus, in one embodiment process 100 may result in a new protocol that is based on a like exam or a similarity metric as the starting point and which is optimized using either a computer based or a human-based optimization, and stored without an exam being performed. However, in another embodiment, a scan may be performed, either using an already-existent scan (block 116) or after conducting an optimization (using human or computer based optimization criteria), at block 140. It is contemplated, however, that at block 140 the scanning may be foregone and control may simply pass to block 142 to determine whether to generate a new protocol or not.

Referring back to step 116, as summarized, if the scan is not optimized 118, then the subsequent steps (either computer or user-selected protocols) result in a new protocol being generated based on a dose optimization. However, if the scan is already determined to be optimized 152, then a new protocol is not generated (and there would thereby be no new exam for storage in the database of the library of exams), in which, as stated, no new protocol is generated 146, and the process simply ends 148 without storing the protocol.

The discussion above has focused on dose modulation assuming that the tube spectrum is relatively stable throughout the acquisition and single energy image reconstruction is utilized. In the case of spectral imaging (achieved either through changing spectrum (e.g. rotate/rotate, multi-tube or fast kVp switching) or different detection methods (e.g. multi-layer detectors or photon counting detectors with discriminating logic) there is an additional degree of freedom which is dose partitioning. For instance in many of these acquisitions there are degrees of freedom such as dwell time at different tube potentials, choice of tube potentials, level of additional filtration, or energy discrimination levels. In each case these parameters can be optimized either for a given task or set of tasks or through a computer interface as described for the single energy dose deposition optimization. In this case a different method to simulate the dose delivery which uses a dual energy acquisition can be utilized.

Different known methods may be used for image reconstruction. Because there is an interaction between the image reconstruction algorithm and the final image quality, in each case it is expected that either the complete image reconstruction algorithm or some acceptable surrogate is used in the image reconstruction step for the procedure described above for optimal dose deposition parameter selection. Further, the simulation techniques discussed may be applied at scan time based on scout images, but may also be applied during the generation of protocols based on parameters such as the body part being imaged and the size of the object being imaged.

In addition protocols may be built explicitly for different given clinical tasks. In this case the task function such as tumor detection, tumor sizing, or vessel sizing may be incorporated into the objective function to find the optimal dose distribution for a given task and to find the minimum possible dose for a given performance level. During the development of protocols the results from similar clinical tasks the results from one set of tuning for a given anatomical location can be used to inform initial parameter selection for another location (e.g. bone imaging in the wrist may be used to inform the initial selection of parameters for bone imaging in the ankle).

Because this simulation environment can be run at either protocol management time or at scan time, there may also be a mechanism incorporated to determine when scan time interactions could be most helpful (i.e., normally use the protocols built ahead of time, but recommend for the special cases that a real time simulation could be beneficial). The special cases may include large variations from the conditions under which the protocol was constructed, such as off center patient positioning, incorporation of implanted hardware, etc.

Figure 6:
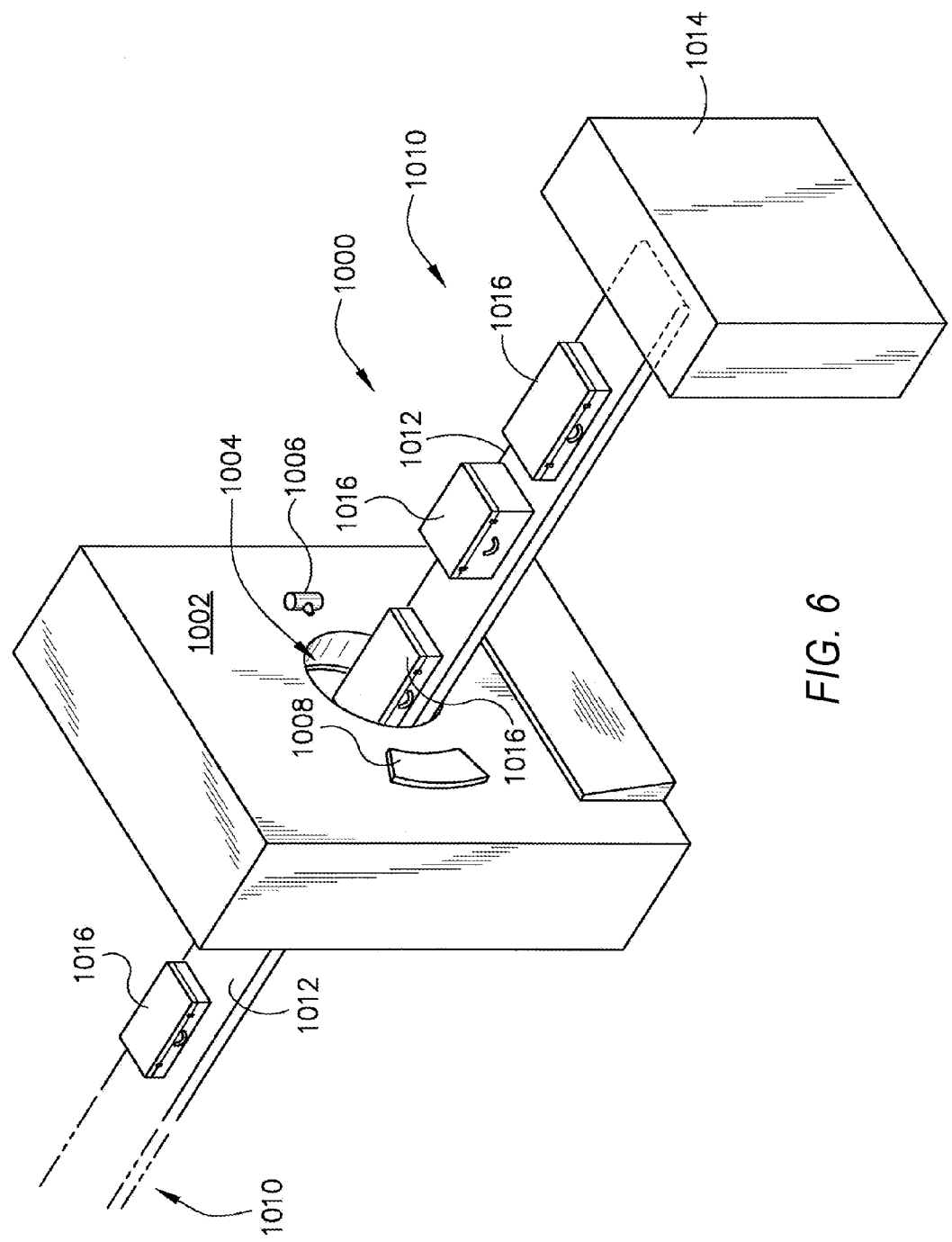
FIG. 6 is a pictorial view of a CT system for use with a non-invasive package inspection system.

Referring now to FIG. 6, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, an imaging system allows for modification of data acquisition parameters, where the parameters affect dose distribution. The system includes a library of exams, and a computer programmed to obtain a set of scanning parameters for image data acquisition and image reconstruction, obtain scan data from the library of exams that is based on a similarity metric for a patient to be scanned, simulate a new scan of the patient using the obtained scan data and using the obtained set of scanning parameters, and generate a new set of scanning parameters based on the simulation.

According to another embodiment, a method of optimizing scanning parameters for image data acquisition includes selecting a scanning protocol for image data acquisition and image reconstruction, obtaining scan data from a library of exams that is based on a similarity metric for a patient to be scanned, determining whether the scanning protocol achieves a desired optimization by simulating a scan of the patient that is based on the selected scanning protocol and based on the obtained scan data, and generating a new scanning protocol based on the optimization.

According to yet another embodiment, a non-transitory computer readable storage medium having stored thereon a computer program comprising instructions, which, when executed by a computer, cause the computer to select a scanning protocol for image data acquisition and image reconstruction, obtain scan data from a library of exams that is based on a similarity metric for a patient to be scanned, determine whether the scanning protocol achieves a desired optimization by simulating a scan of the patient that is based on the selected scanning protocol and based on the obtained scan data, and generate a new scanning protocol based on the optimization.

A technical contribution for the disclosed method and apparatus is that it provides for a computer-implemented apparatus and method to optimize a scanning protocol to minimize dose, based on specifics of the patient and the conditions under which the scanning protocol are implemented.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. An imaging system that allows for modification of data acquisition parameters, where the parameters affect dose distribution, comprising:
    a library of exams, wherein the library of exams comprises a plurality of scans from different patients; and
    a computer programmed to:
        obtain a set of scanning parameters for image data acquisition and image reconstruction;
        select a scan from among the plurality of scans from the library of exams based on a similarity metric for a patient to be scanned and obtain scan data from the scan;
        simulate a new scan of the patient using the obtained scan data and using the obtained set of scanning parameters; and
        generate a new set of scanning parameters based on the simulation.

2. The imaging system of claim 1, wherein the similarity metric is based on one of a 2D scout and a 3D scout.

3. The imaging system of claim 1, wherein the similarity metric is based on one of a patient weight, a body mass index (BMI), and a patient circumference.

4. The imaging system of claim 1, wherein the computer is further programmed to enable optimization of the scanning parameters based on the simulation, and generate the new set of scanning parameters based on the optimization.

5. The imaging system of claim 4, wherein the computer is further programmed to optimize the scanning parameters based on at least one of:
    A) dose reduction
    B) dose reduction to a particular area of anatomy;
    C) object detectability;
    D) noise reduction in at least one region;
    E) noise uniformity in at least one region; and
    F) image quality.

6. The imaging system of claim 4, wherein the computer is further programmed to enable a user to change the scanning parameters, and simulate the new scan using the changed parameters.

7. The imaging system of claim 4, wherein the computer is further programmed to automatically change scanning parameters, and simulate the new scan using the automatically changed parameters.

8. The imaging system of claim 4, wherein the computer is further programmed to request user confirmation of the new scanning parameters, and:
    if confirmed, then select the new scanning parameters; and
    if not confirmed, then offer the user an opportunity to determine another set of scanning parameters.

9. The imaging system of claim 4, wherein, if confirmed and the patient is scanned with the new set of scanning parameters, the computer is programmed to save results of the scan and the corresponding scanning parameters to the library of exams.

10. The imaging system of claim 1, wherein the computer is further programmed to obtain the set of scanning parameters by requesting a user to select the scanning parameters.

11. A method of optimizing scanning parameters for image data acquisition, comprising:
    selecting a scanning protocol for image data acquisition and image reconstruction;
    select a scan from among a plurality of scans from a library of exams based on a similarity metric for a patient to be scanned and obtain scan data from the scan, wherein the library of exams comprises the plurality of scans from different patients;
    determining whether the scanning protocol achieves a desired optimization by simulating a new scan of the patient that is based on the selected scanning protocol and based on the obtained scan data; and
    generating a new scanning protocol based on the optimization.

12. The method of claim 11, wherein the similarity metric is based on:
    one of a 2D scout and a 3D scout; or one of a patient weight, a body mass index (BMI), and a patient circumference.

13. The method of claim 11, further comprising optimizing the scanning protocol by varying at least one parameter of the scanning protocol and simulating the new scan of the patient using the variation of the at least one parameter.

14. The method of claim 13, further comprising determining the optimal dose deposition based at least in part on one of:
    A) dose reduction
    B) dose reduction to a particular area of anatomy;
    C) object detectability;
    D) noise reduction in at least one region;
    E) noise uniformity in at least one region; and
    F) image quality.

15. The method of claim 13, further comprising one of:
varying the at least one parameter of the scanning protocol by enabling a user to manually vary the at least one parameter, and simulating the new scan of the patient using the variation of the at least one parameter; and
automatically varying the at least one parameter of the scanning protocol using a computer, and simulating the new scan of the patient using the variation of the at least one parameter.

16. The method of claim 15, wherein the method further includes one of:
A) selecting the new scanning protocol, and offering the selected protocol to a user and presenting an opportunity to override the selected protocol and select a different protocol; and
B) presenting results of the simulated scan to the user, and offering the user an opportunity to modify scan parameters in real-time; and presenting the simulation of the new scan to the user so the user can view the modified simulation and modify the scan parameters to generate the new scanning protocol based on the modified simulation.

17. A non-transitory computer readable storage medium having stored thereon a computer program comprising instructions, which, when executed by a computer, cause the computer to:
select a scanning protocol for image data acquisition and image reconstruction;
select a scan from among a plurality of scans from a library of exams based on a similarity metric for a patient to be scanned and obtain scan data from the scan, wherein the library of exams comprises the plurality of scans from different patients;
determine whether the scanning protocol achieves a desired optimization by simulating a new scan of the patient that is based on the selected scanning protocol and based on the obtained scan data; and
generate a new scanning protocol based on the optimization.

18. The non-transitory computer readable storage medium of claim 17, wherein the similarity metric is based on:
one of a 2D scout and a 3D scout; or
one of a patient weight, a body mass index (BMI), and a patient circumference.

19. The non-transitory computer readable storage medium of claim 17, wherein the computer is further caused to optimize the scanning protocol by varying at least one parameter of the scanning protocol, and simulate the new scan of the patient using the variation of the at least one parameter.

20. The non-transitory computer readable storage medium of claim 17, wherein the computer is further caused to:
vary the at least one parameter of the scanning protocol by enabling a user to manually vary the at least one parameter, and simulating the new scan of the patient using the variation of the at least one parameter; or
automatically vary the at least one parameter of the scanning protocol using a computer, and simulating the new scan of the patient using the variation of the at least one parameter.

* * * * *